(12) United States Patent
Chen

(10) Patent No.: US 11,826,581 B2
(45) Date of Patent: Nov. 28, 2023

(54) LIGHT SUPPLY METHOD FOR SLEEP AID

(71) Applicant: National Taiwan University of Science and Technology, Taipei (TW)

(72) Inventor: Chien-Yu Chen, Taipei (TW)

(73) Assignee: National Taiwan University of Science and Technology, Taipei (TW)

(*) Notice: Subject to any disclaimer, the term of this patent is extended or adjusted under 35 U.S.C. 154(b) by 745 days.

(21) Appl. No.: 16/850,002

(22) Filed: Apr. 16, 2020

(65) Prior Publication Data
US 2020/0330788 A1    Oct. 22, 2020

Related U.S. Application Data

(60) Provisional application No. 62/834,980, filed on Apr. 17, 2019.

(51) Int. Cl.
*A61N 5/06* (2006.01)
*A61M 21/02* (2006.01)
*G16H 40/63* (2018.01)

(52) U.S. Cl.
CPC .......... *A61N 5/0618* (2013.01); *A61M 21/02* (2013.01); *G16H 40/63* (2018.01); *A61N 2005/0629* (2013.01); *A61N 2005/0663* (2013.01)

(58) Field of Classification Search
CPC .......... A61N 5/0618; A61N 2005/0629; A61N 2005/0663; A61M 21/02; A61M 2021/0044; G16H 40/63; G16H 20/70
USPC .................................................. 600/26–28
See application file for complete search history.

(56) References Cited

U.S. PATENT DOCUMENTS

| | | | |
|---|---|---|---|
| 2010/0171441 A1* | 7/2010 | Schlangen | A61M 21/00 315/294 |
| 2011/0084614 A1* | 4/2011 | Eisele | H05B 47/155 315/297 |
| 2012/0095534 A1* | 4/2012 | Schlangen | A61M 21/00 607/90 |
| 2014/0052220 A1* | 2/2014 | Pedersen | A61M 21/00 607/88 |
| 2016/0273717 A1* | 9/2016 | Krames | G02F 1/133603 |
| 2017/0080246 A1* | 3/2017 | Knight | A61G 10/02 |
| 2017/0105265 A1* | 4/2017 | Sadwick | H05B 47/11 |

(Continued)

FOREIGN PATENT DOCUMENTS

| | | |
|---|---|---|
| TW | 201319709 | 5/2013 |
| TW | 201818783 | 5/2018 |
| TW | M588935 | 1/2020 |

OTHER PUBLICATIONS

"Office Action of Taiwan Counterpart Application", dated Nov. 26, 2020, p. 1-p. 3.

*Primary Examiner* — Sunita Reddy
(74) *Attorney, Agent, or Firm* — JCIPRNET

(57) ABSTRACT

A light supply method is provided. The light supply method includes: providing a first driving signal in a first time interval by a driver and providing a first time-varying light by a light source module in response to the first driving signal; providing a second driving signal in a second time interval after the first time interval by the driver and providing a first fixed light by the light source module in response to the second driving signal; and providing a third driving signal by the driver in a third time interval after the second time interval and providing a second time-varying light by the light source module in response to the third driving signal.

18 Claims, 9 Drawing Sheets

(56) References Cited

U.S. PATENT DOCUMENTS

| | | | |
|---|---|---|---|
| 2017/0189640 A1* | 7/2017 | Sadwick | H05B 45/20 |
| 2018/0020523 A1* | 1/2018 | Desouches | H05B 47/155 |
| 2018/0077767 A1* | 3/2018 | Soler | H05B 45/20 |
| 2018/0250493 A1* | 9/2018 | Kido | H05B 47/16 |
| 2018/0339127 A1* | 11/2018 | Van Reen | A61N 5/0618 |
| 2019/0192878 A1* | 6/2019 | Lang | A61N 5/0618 |
| 2019/0209806 A1* | 7/2019 | Allen | G16H 40/67 |
| 2021/0045220 A1* | 2/2021 | Barna | H05B 47/19 |
| 2021/0162912 A1* | 6/2021 | Spero | H05B 45/395 |

* cited by examiner

LIGHT SUPPLY METHOD FOR SLEEP AID

CROSS-REFERENCE TO RELATED APPLICATION

This application claims the priority benefit of U.S. provisional application Ser. No. 62/834,980, filed on Apr. 17, 2019. The entirety of the above-mentioned patent application is hereby incorporated by reference herein and made a part of this specification.

BACKGROUND OF THE INVENTION

1. Field of the Invention

The invention relates to a light supply method, in particular to a light supply method for sleep aid.

2. Description of Related Art

Sleep insufficiency is a common problem, which affects health, spirit, mood and behavior throughout the day. Insomnia may even cause serious problems. The insomnia results in that many people cannot sleep continuously or fall asleep. Insomniac people may usually have mental inattention, fatigue, impaired concentration, emotional instability and task performance decline. Many people try to use drugs for treatment, but it may cause adverse side effects. Therefore, how to effectively improve sleep is one of the subjects that those skilled in the art strive to study.

SUMMARY OF THE INVENTION

The invention provides a light supply method for sleep aid.

The light supply method of the invention is suitable for an electronic device. The electronic device includes a driver and a light source module. The light supply method includes the following steps. A first driving signal is provided in a first time interval by the driver and a first time-varying light is provided by the light source module in response to the first driving signal; a second driving signal is provided in a second time interval after the first time interval by the driver and a first fixed light is provided by the light source module in response to the second driving signal, wherein the first time-varying light is gradually changed into the first fixed light at the end of the first time interval; and a third driving signal is provided by the driver in a third time interval after the second time interval and a second time-varying light is provided by the light source module in response to the third driving signal.

Based on the above, the light supply method of the invention provides the first time-varying light, the first fixed light and the second time-varying light periodically and sequentially. Thus, the light supply method of the invention can realize a technical effect of sleep aid, thereby further improving a mental state, a concentration degree, and working efficiency of a user, etc.

To make the features and advantages of the invention clear and easy to understand, the following gives a detailed description of embodiments with reference to accompanying drawings.

DESCRIPTION OF THE EMBODIMENTS

Part of embodiments of the invention will be described in detail next in combination with the drawings. Component symbols to which reference is made in the following descriptions will be regarded as the same or similar components when the same component symbol appears in the different drawings. These embodiments are only a part of the invention and do not disclose all implementable modes of the invention. To be more exact, these embodiments are only examples of devices and methods within patent claims of the invention.

Figure 1:
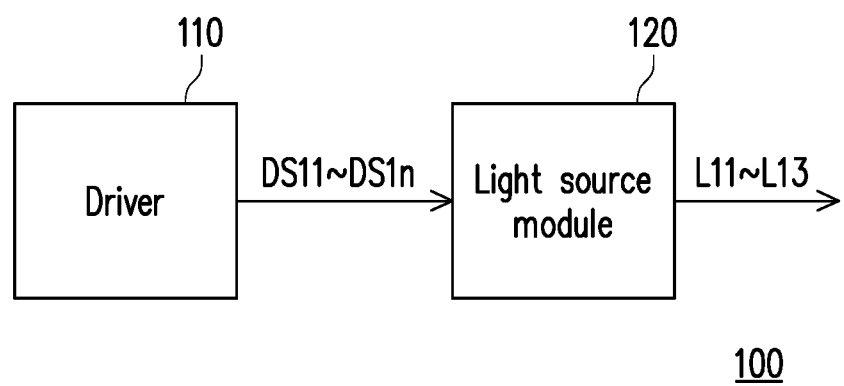
FIG. 1 is a schematic diagram of an electronic device drawn according to a first embodiment of the invention.
Figure 2:
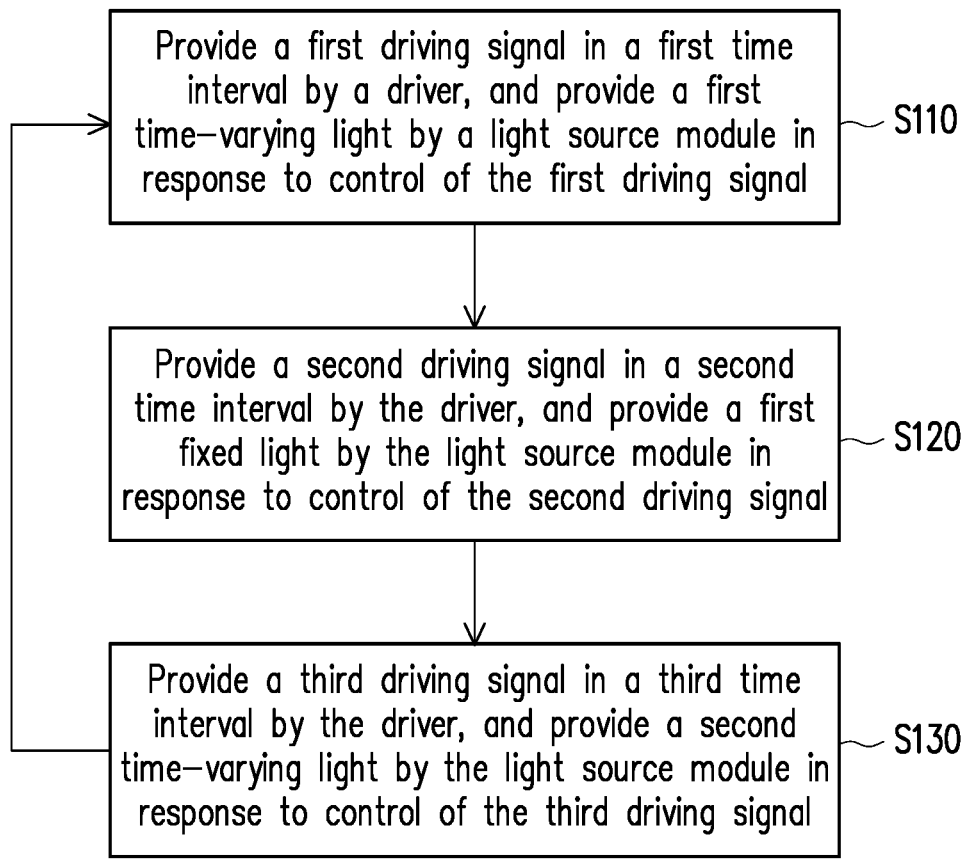
FIG. 2 is a method flow chart of a light supply method drawn according to the first embodiment of the invention.

Referring to FIG. 1 and FIG. 2 at the same time, FIG. 1 is a schematic diagram of an electronic device drawn according to a first embodiment of the invention. FIG. 2 is a method flow chart of a light supply method drawn according to the first embodiment of the invention. In the present embodiment, the electronic device 100 includes a driver 110 and a light source module 120. The driver 110 provides driving signals DS11 to DS1$n$ periodically and sequentially. The light source module 120 provides corresponding lights in response to the driving signals DS11 to DS1$n$. Therefore, the light source module 120 provides the plurality of lights periodically. The electronic device 100 may be a lamp, a cell phone, a tablet computer, a notebook computer, or a desktop computer, etc. The light source module 120 may be implemented by a plurality of light-emitting diodes (LEDs) of any type, or implemented by displayers of any type. In the present embodiment, each period has a plurality of time intervals.

In step S110, the driver 110 provides the driving signal DS11 in a first time interval. The light source module 120 provides a first time-varying light L11 in response to the driving signal DS11. In step S120, the driver 110 provides the driving signal DS12 in a second time interval after the first time interval. The light source module 120 provides a first fixed light L12 in response to the driving signal DS12. In the present embodiment, the first time-varying light L11 is gradually changed into the first fixed light L12 at the end of the first time interval. In step S130, the driver 110 provides the driving signal DS13 in a third time interval after the second time interval. The light source module 120 provides a second time-varying light L13 in response to the driving signal DS13. In a next period, the driver 110 returns to step S120 so as to provide a driving signal DS11 in a first time interval, and so on.

It is worth mentioning herein that the light supply method provides the first time-varying light L11, the first fixed light L12 and the second time-varying light L13 periodically and sequentially. The light supply method of the present embodiment can provide the various lights periodically and utilizes the first time-varying light L11 and the second time-varying light L13 to provide periodic light variations. Through experiments, the activity of slow waves in brain waves of a user is improved to realize a technical effect of sleep aid, which further improves sleep quality. Furthermore, by applying the first time-varying light and the second time-varying light, it may be conductive to inducing theta (θ) waves and delta (δ) waves in the brain waves of the user. During sleeping, enhancement of the theta waves means that the user enters into a rapid eye movement stage, and enhancement of the delta waves means that the user enters into a non-rapid eye movement stage. Thus, the present embodiment can make the user fall asleep rapidly and improve the sleep quality, and improves a mental state, a concentration degree, and working efficiency of the user, etc.

Figure 3:
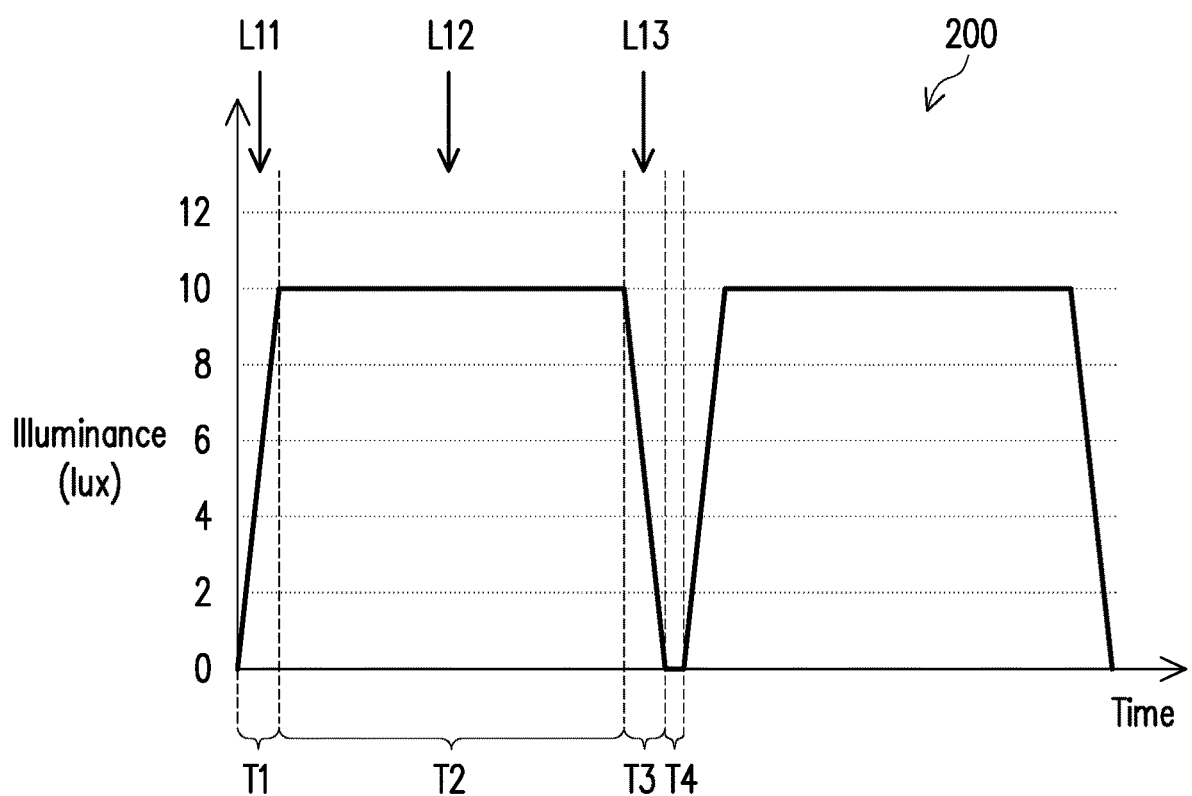
FIG. 3 is an illuminance variation diagram drawn according to a second embodiment of the invention.
Figure 4:
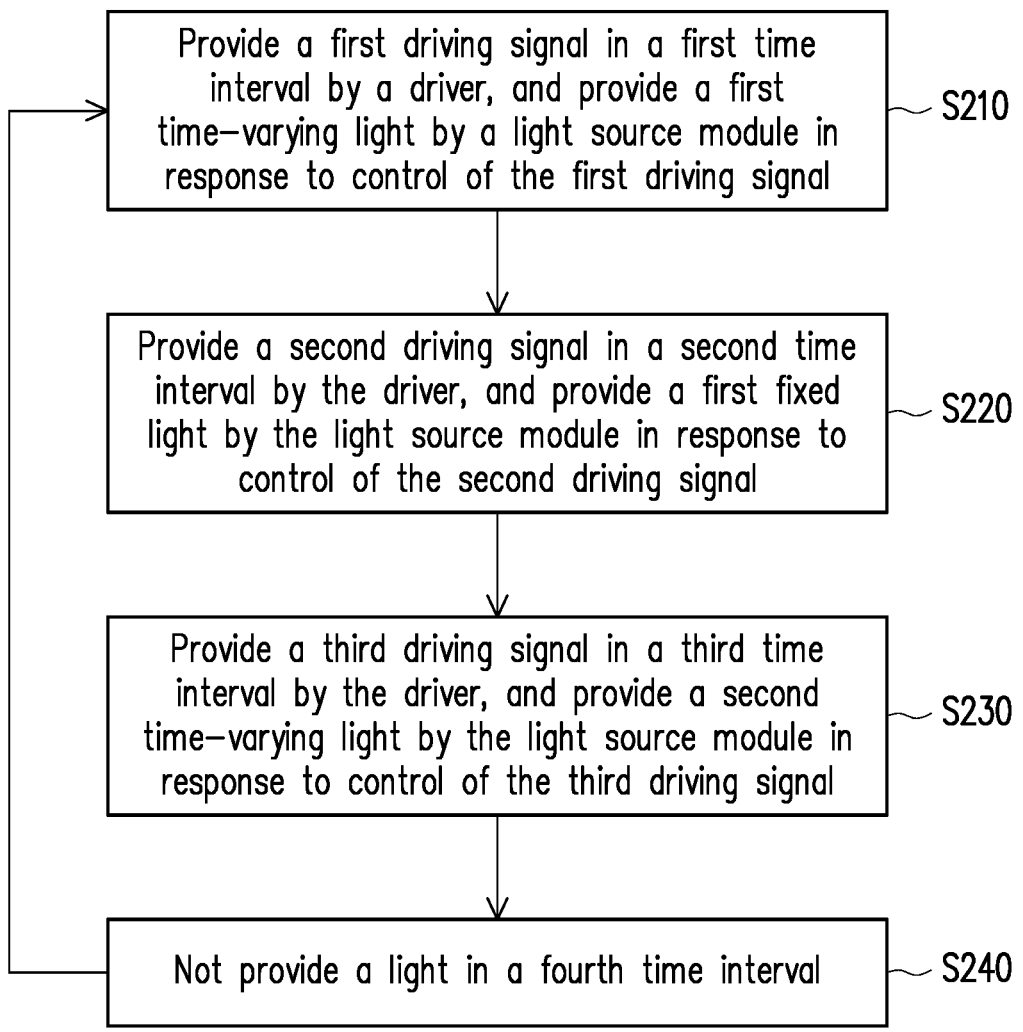
FIG. 4 is a method flow chart of a light supply method drawn according to the second embodiment of the invention.

For example, referring to FIG. 1, FIG. 3 and FIG. 4 at the same time, FIG. 3 is an illuminance variation diagram drawn according to a second embodiment of the invention. FIG. 4 is a method flow chart of a light supply method drawn according to the second embodiment of the invention. Illuminance variations of the illuminance variation diagram 200 of the present embodiment are suitable for the first embodiment. Illuminance is a light flux per unit area of the lights provided by the light source module 120 projected on a target object (such as a user). Therefore, the above-mentioned [illuminance variations] are variations related to the light flux of the lights provided by the light source module 120 projected on the user. In step S210, the light source module 120 provides a first time-varying light L11 in a first time interval T1 in response to a driving signal DS11. Illuminance generated by the first time-varying light L11 is linearly increased with time. For example, based on driving of the driving signal DS11, the illuminance generated by the first time-varying light L11 is increased at a speed of 3 to 10 lux per second.

In step S220, the light source module 120 provides a first fixed light L12 in a second time interval T2 in response to a driving signal DS12. Illuminance generated by the first fixed light L12 is maintained between 9 lux and 11 lux. For example, based on driving of the driving signal DS12, the illuminance generated by the first fixed light L12 is maintained at 10 lux. Therefore, the first time-varying light L11 is gradually changed to be 10 lux at the end of the first time interval T1 so as to be turned into the first fixed light L12 at the beginning of the second time interval T2.

In step S230, the light source module 120 provides a second time-varying light L13 in a third time interval T3 in response to a driving signal DS13. Illuminance generated by the second time-varying light L13 is linearly decreased with time. For example, based on driving of the driving signal DS13, the illuminance generated by the second time-varying light L13 is decreased at a speed of 3 to 10 lux per second.

In the present embodiment, illuminance variations generated by the first time-varying light L11 and the second time-varying light L13 can be set. For example, a user (such as an elder) with poor light sensitivity is taken as a using object. The illuminance variation of the first time-varying light L11 can be set to be increased by 8 to 10 lux per second, and the illuminance variation of the second time-varying light L13 can be set to be decreased by 8 to 10 lux per second, so as to improve the sleep aid effect.

In step S240, the light source module 120 is controlled not to provide a light in a fourth time interval T4 between the third time interval T3 and a first time interval of a next period. Therefore, illuminance generated by the light source module 120 in the fourth time interval T4 is 0 lux. In the present embodiment, the illuminance generated by the second time-varying light L13 is decreased to 0 lux at the end of the third time interval T3.

In the present embodiment, a time length of a period is set to be 30 minutes. That is, a sum of time lengths of the first time interval T1, the second time interval T2, the third time interval T3 and the fourth time interval T4 is substantially equal to 30 minutes.

In the present embodiment, a color temperature of the first time-varying light L11, a color temperature of the second time-varying light L13, and a color temperature of the first fixed light L12 are maintained at 1900±100 k. That is, the color temperature of the first time-varying light L11, the color temperature of the second time-varying light L13 and the color temperature of the first fixed light L12 are maintained between 1800 k and 2000 k.

In some embodiments, the electronic device 100 can sense the color temperature and the illuminance so as to judge whether the illuminance and color temperature generated by the first time-varying light L11, the illuminance and color temperature generated by the second time-varying light L13 and the illuminance and color temperature generated by the first fixed light L12 offset or not. The electronic device 100 corrects offset lights once judging that the above-mentioned illuminance or color temperatures offset.

Figure 5:
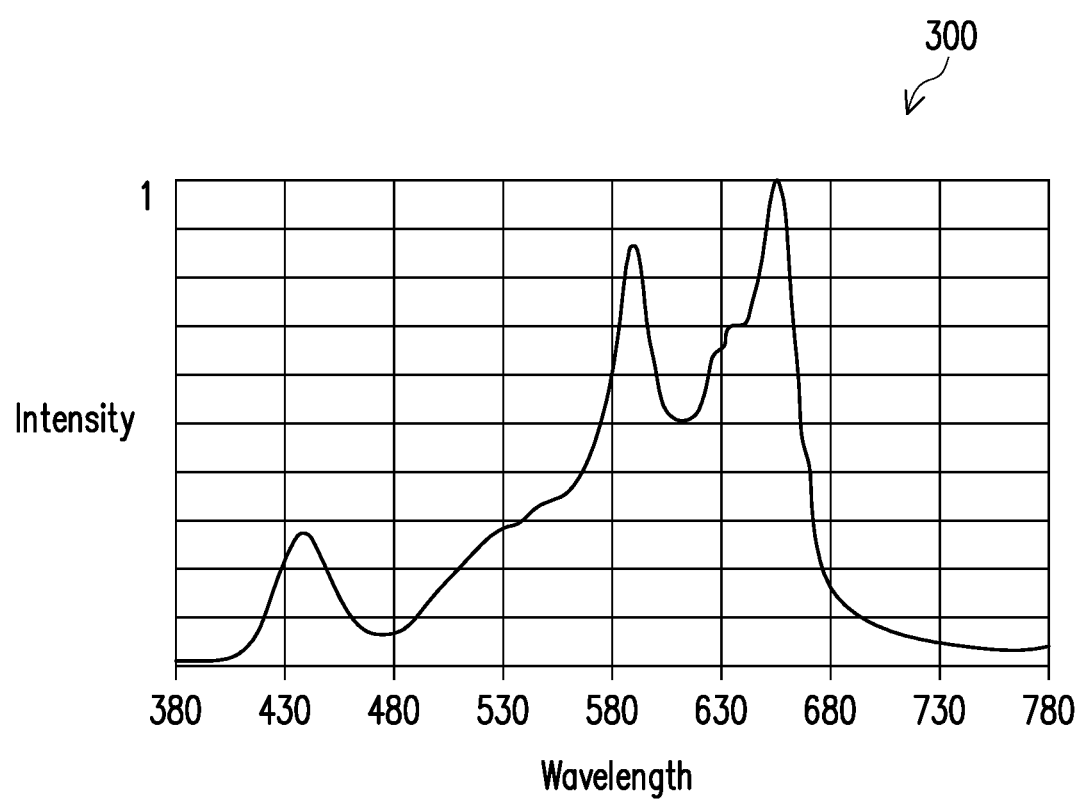
FIG. 5 is a light spectrogram drawn according to one embodiment of the invention.

Referring to FIG. 1 and FIG. 5 at the same time, FIG. 5 is a light spectrogram drawn according to one embodiment of the invention. Intensities in the light spectrogram 300 are normalized. A spectrum of the light spectrogram 300 is suitable for the first time-varying light L11, the second time-varying light L13 and the first fixed light L12. Therefore, in the present embodiment, intensities of lights within a wavelength range shorter than 455 nanometers are reduced. Thus, the electronic device 100 does not restrain secretion of melatonin, which further improves the sleep quality of a user. In addition, according to research, a blue light with a wavelength being within 415 to 455 nanometers will damage a retina. Therefore, the electronic device 100 will also reduce damage to the retina.

Figure 6:
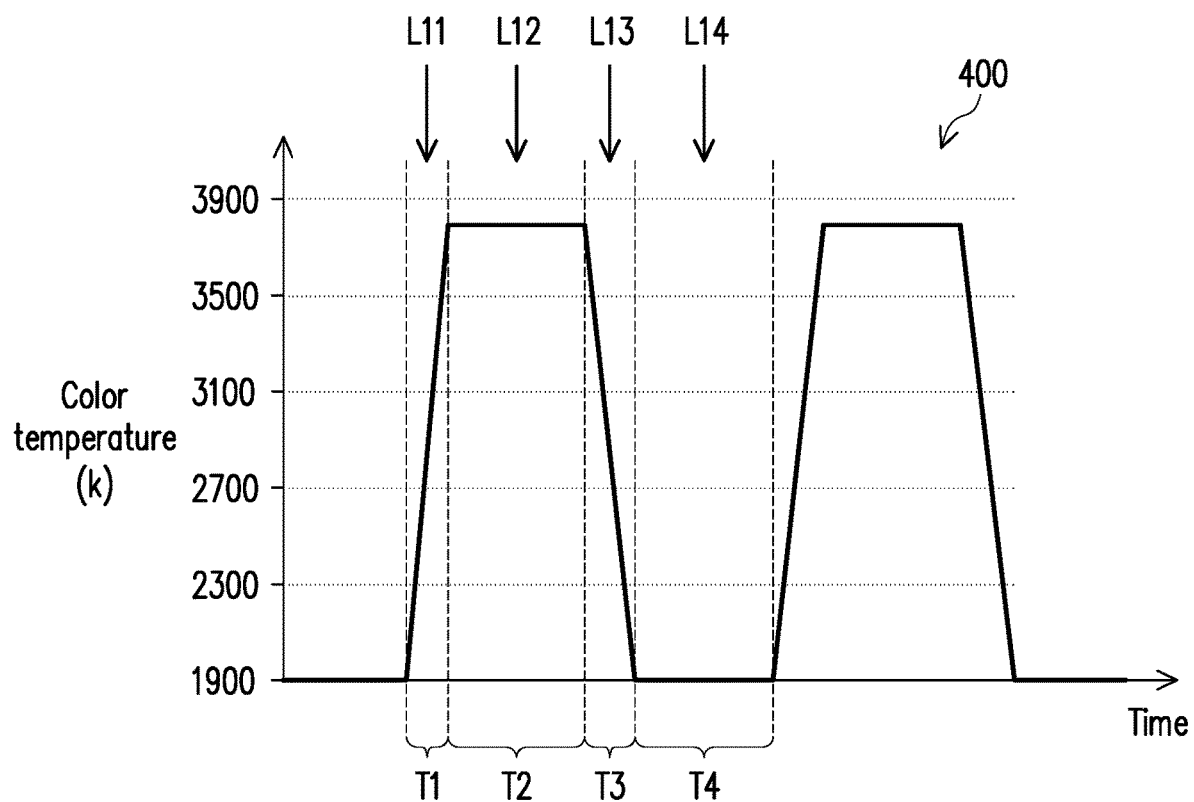
FIG. 6 is a color temperature variation diagram drawn according to a third embodiment of the invention.
Figure 7:
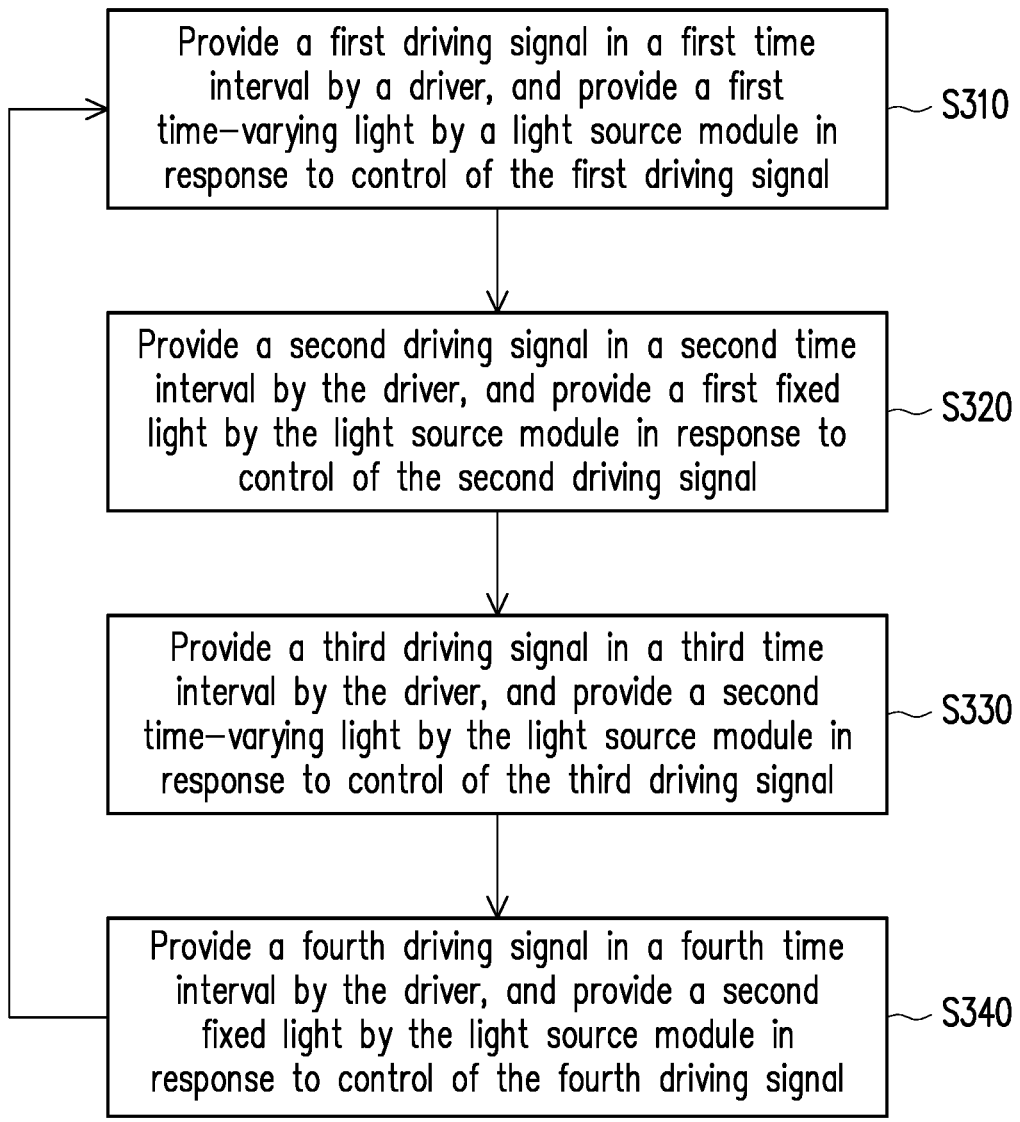
FIG. 7 is a method flow chart of a light supply method drawn according to the third embodiment of the invention.

For example, referring to FIG. 1, FIG. 6 and FIG. 7 at the same time, FIG. 6 is a color temperature variation diagram drawn according to a third embodiment of the invention. FIG. 7 is a method flow chart of a light supply method drawn according to the third embodiment of the invention. Color temperature variations of the color temperature variation diagram 400 of the present embodiment are suitable for the first embodiment. In step S310, the light source module 120 provides a first time-varying signal L11 in a first time interval T1 in response to a driving signal DS11. A color temperature of the first time-varying signal L11 is linearly increased with time. For example, based on driving of the driving signal DS11, the color temperature of the first time-varying signal L11 is increased at a speed of 50 to 200 k per second.

In step S320, the light source module 120 provides a first fixed light L12 in a second time interval T2 in response to a driving signal DS12. A color temperature of the first fixed light L12 is maintained between 3600 k and 5000 k. For example, based on driving of the driving signal DS12, the color temperature of the first fixed signal L12 is maintained at 3800 k. Therefore, the color temperature of the first time-varying light L11 is gradually changed to be 3800 k at the end of the first time interval T1, so that the first time-varying light is turned into the first fixed light L12 at the beginning of the second time interval T2.

In step S330, the light source module 120 provides a second time-varying signal L13 in a third time interval T3 in response to a driving signal DS13. A color temperature of the second time-varying signal L13 is linearly decreased with time. For example, based on driving of the driving signal DS13, the color temperature of the second time-varying signal L13 is decreased at a speed of 50 to 200 k per second.

In step S340, the driver 110 further provides a driving signal DS14 in a fourth time interval T4. The light source module 120 provides a second fixed light L14 in response to the driving signal DS14. A color temperature of the second fixed light L14 is maintained between 1600 k and 2400 k. For example, based on driving of the driving signal DS14, the color temperature of the second fixed signal L14 is maintained at 1900 k. Therefore, the color temperature of the second time-varying light L13 is gradually changed to be 1900 k at the end of the third time interval T3, so that the second time-varying light is turned into the second fixed light L14 at the beginning of the fourth time interval T4. In the present embodiment, a time length of the first time interval T1 and a time length of the fourth time interval T4 are set to be 30 minutes. The light supply method of the present embodiment utilizes the first time-varying light and the second time-varying light to provide periodic color temperature variations, so that the activity of slow waves in brain waves of a user is improved (for example, the delta (δ) waves are enhanced) to realize the technical effect of sleep aid, which further improves the sleep quality.

In the present embodiment, illuminance generated by the first time-varying light L11, illuminance generated by the second time-varying light L13, illuminance generated by the first fixed light L12, and illuminance generated by the second fixed light L14 are maintained at 51±1 lux. That is, the illuminance generated by the first time-varying light L11, the illuminance generated by the second time-varying light L13, the illuminance generated by the first fixed light L12, and the illuminance generated by the second fixed light L14 are maintained between 50 lux and 52 lux.

In the present embodiment, color temperature variations of the first time-varying light L11 and the second time-varying light L13 can be set. For example, a user (such as an elder) with poor light sensitivity is taken as a using object. The color temperature variation of the first time-varying light L11 can be set to be increased by 150 to 200 k per second, and the color temperature variation of the second time-varying light L13 can be set to be decreased by 150 to 200 k per second, so as to improve the sleep aid effect. For another example, a user (such as a youngster) with good light sensitivity is taken as a using object. The color temperature variation of the first time-varying light L11 can be set to be increased by 50 to 200 k per second, and the color temperature variation of the second time-varying light L13 can be set to be decreased by 50 to 200 k per second.

Figure 8:
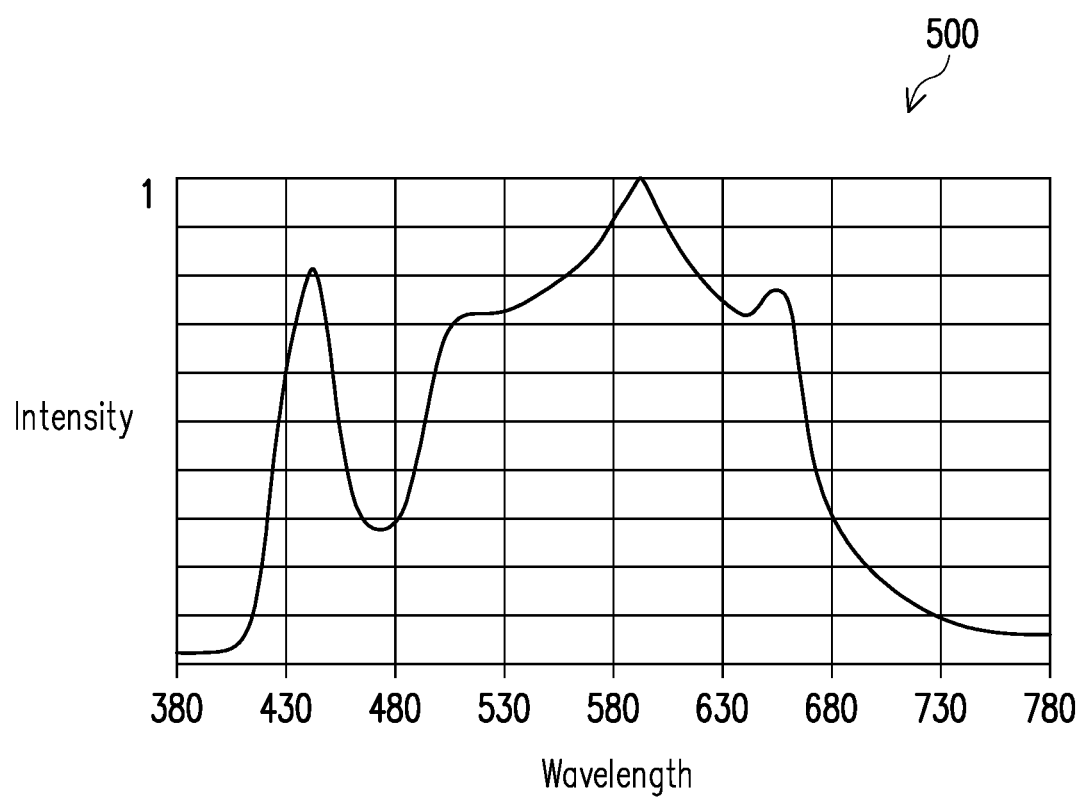
FIG. 8 is a light spectrogram of a first fixed light drawn according to one embodiment of the invention.

Referring to FIG. 1, FIG. 5 and FIG. 8 at the same time, FIG. 8 is a light spectrogram of a first fixed light drawn according to one embodiment of the invention. Intensities in the light spectrogram 500 are normalized. In the present embodiment, a spectrum of the light spectrogram 500 is suitable for a first fixed light L12 of the present embodiment. The spectrum of the light spectrogram 300 shown in FIG. 5 is suitable for a second fixed light L14 of the present embodiment. Similar to the light spectrogram 300, in the light spectrogram 500 of the present embodiment, intensities of lights within a wavelength range shorter than 455 nanometers are also reduced. But a reducing amount of the intensities of the lights within the wavelength range shorter than 455 nanometers in the light spectrogram 500 is lower than that of the intensities of the lights within the wavelength range shorter than 455 nanometers in the light spectrogram 300. Therefore, the intensities of the lights within the wavelength range shorter than 455 nanometers in the light spectrogram 500 are greater than the intensities of the lights within the wavelength range shorter than 455 nanometers in the light spectrogram 300. In addition, intensities of lights within a wavelength range longer than 630 nanometers in the light spectrogram 500 are less than intensities of lights within a wavelength range longer than 630 nanometers in the light spectrogram 300. Therefore, a color temperature presented in the light spectrogram 500 is obviously higher than a color temperature presented in the light spectrogram 300.

In the present embodiment, a spectrum of a first time-varying light L11 is gradually changed from the spectrum of the light spectrogram 300 into the spectrum of the light spectrogram 500 in a first time interval, so that the first time-varying light is turned into the first fixed light L12 in a second time interval. A spectrum of a second time-varying light L13 is gradually changed from the spectrum of the light spectrogram 500 into the spectrum of the light spectrogram 300 in a third time interval, so that the second time-varying light is turned into the second fixed light L14 in a fourth time interval.

Figure 9:
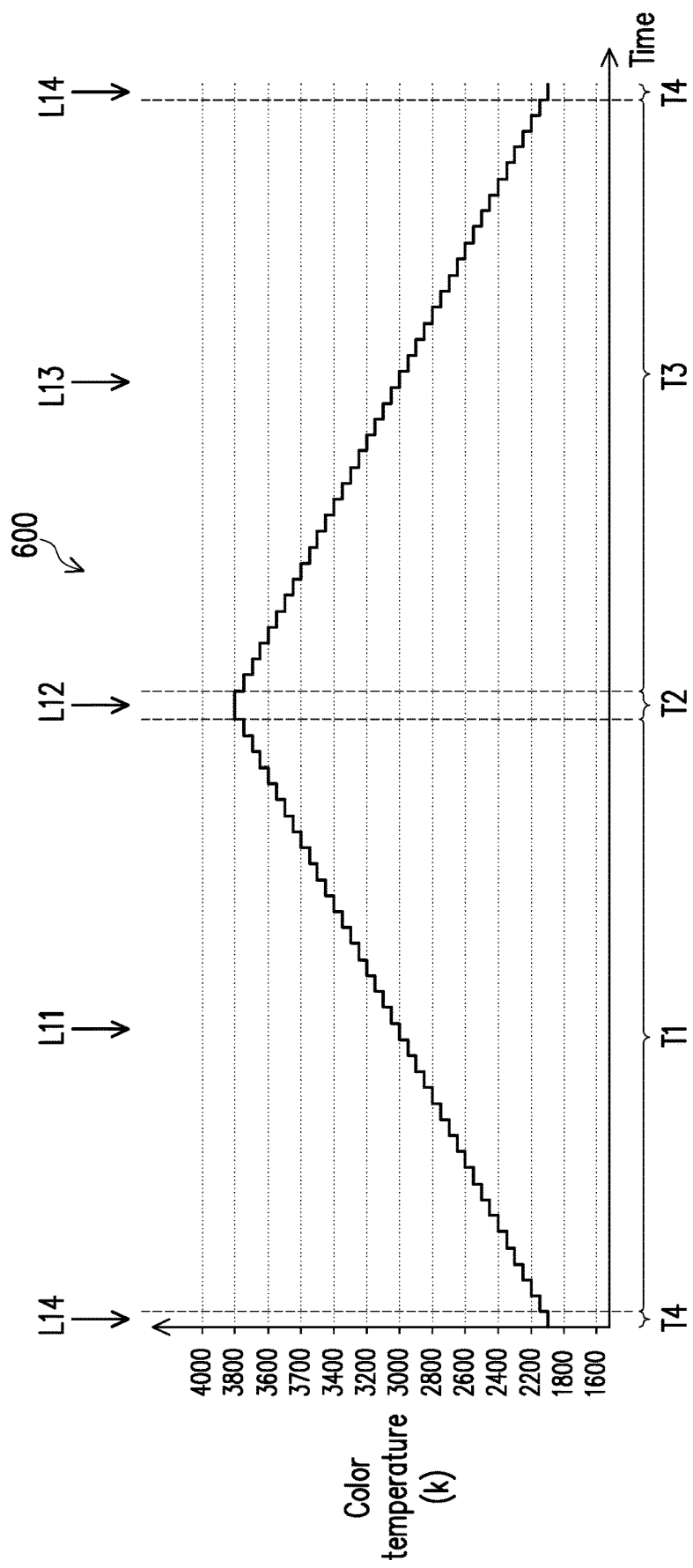
FIG. 9 is a color temperature variation diagram drawn according to a fourth embodiment of the invention.

For example, referring to FIG. 1, FIG. 7 and FIG. 9 at the same time, FIG. 9 is a color temperature variation diagram drawn according to a fourth embodiment of the invention. In the present embodiment, color temperature variations of the color temperature variation diagram 600 of the present embodiment are suitable for the first embodiment. In step S310, a color temperature of a first time-varying light L11 is increased with time in a stepping mode. In the present embodiment, the first time-varying light L11 is increased by 50 to 200 k at each step. In the present embodiment, maintaining time of each step of the first time-varying light L11 is 0.5 to 0.8 seconds.

In step S320, a color temperature of a first fixed light L12 is maintained between 3600 k and 5000 k. For example, the color temperature of the first fixed light L12 is maintained at 3800 k. Therefore, the color temperature of the first time-varying light L11 is turned to be 3800 k at the end of a first time interval T1, so that the first time-varying light is turned into the first fixed light L12 at the beginning of a second time interval T2. In the present embodiment, a time length of the second time interval T2 is greater than or equal to the maintaining time of each step of the first time-varying light L11. For a spectrum of the first fixed light L12, reference may be made to the light spectrogram 300 shown in FIG. 5.

In step S330, a color temperature of a second time-varying light L13 is decreased with time in a stepping mode. In the present embodiment, the second time-varying light L13 is decreased by 50 to 200 k at each step. In the present embodiment, maintaining time of each step of the second time-varying light L13 is 0.5 to 0.8 seconds.

In step S340, a color temperature of a second fixed light L14 is maintained between 1600 k and 2400 k. For example, the color temperature of the second fixed light L14 is maintained at 3800 k. Therefore, the color temperature of the second time-varying light L13 is turned to be 3800 k at the end of a third time interval T3, so that the second time-varying light is turned into the second fixed light L14 at the beginning of a fourth time interval T4. For a spectrum of the second fixed light L14, reference may be made to the light spectrogram 500 shown in FIG. 8. In the present embodiment, a time length of the fourth time interval T4 is greater than or equal to the maintaining time of each step of the first time-varying light L11 and the second time-varying light L13.

In the present embodiment, illuminance generated by the first time-varying light L11, illuminance generated by the second time-varying light L13, illuminance generated by the first fixed light L12, and illuminance generated by the second fixed light L14 are maintained at 51±1 lux.

Similar to the third embodiment, in the present embodiment, color temperature variations of the first time-varying light L11 and the second time-varying light L13 can be set. For example, a user with poor light sensitivity is taken as a using object. The color temperature variation of the first time-varying light L11 can be set to be increased by 150 to 200 k at each step, and the color temperature variation of the second time-varying light L13 can be set to be decreased by 150 to 200 k at each step. For another example, a user with good light sensitivity is taken as a using object. The color temperature variation of the first time-varying light L11 can be set to be increased by 50 to 200 k at each step, and the color temperature variation of the second time-varying light L13 can be set to be decreased by 50 to 200 k at each step. In the present embodiment, a sum of time lengths of the first time interval T1, the second time interval T2, the third time interval T3 and the fourth time interval T4 is roughly equal to 60 seconds.

Based on the above, the light supply method of the invention utilizes the first time-varying light and the second time-varying light to provide the periodic light variations, so that the activity of the slow waves in the brain waves of the user is improved to realize the technical effect of sleep aid, which further improves the sleep quality. Furthermore, by applying the first time-varying light and the second time-varying light, it may be conductive to inducing the theta waves and the delta waves in the brain waves of the user. Thus, the invention can make the user fall asleep rapidly and improve the sleep quality, and improves the mental state, the concentration degree, and the working efficiency of the user, etc.

Although the invention is described with reference to the above embodiments, the embodiments are not intended to limit the invention. A person of ordinary skill in the art may make variations and modifications without departing from the spirit and scope of the invention. Therefore, the protection scope of the invention should be subject to the appended claims.

What is claimed is:

1. A light supply method for sleep aid, configured for an electronic device, wherein the electronic device comprises a driver and a light source module, the light supply method comprising:
    providing a first driving signal in a first time interval by the driver and providing a first time-varying light by the light source module in response to the first driving signal;
    providing a second driving signal in a second time interval after the first time interval by the driver and providing a first fixed light by the light source module in response to the second driving signal, wherein the first time-varying light is gradually changed into the first fixed light upon the first time interval ending; and
    providing a third driving signal by the driver in a third time interval after the second time interval and providing a second time-varying light by the light source module in response to the third driving signal,
    wherein a color temperature of the first time-varying light is increased with time in a stepping mode, and a color temperature of the second time-varying light is decreased with time in the stepping mode, wherein the first time-varying light is increased by 50 Kelvin (K) to 200 K at each step, and wherein a maintaining time of the each step of the first time-varying light is 0.5 seconds to 0.8 seconds.

2. The light supply method according to claim 1, wherein illuminance generated by the first time-varying light is linearly increased with time, and illuminance generated by the second time-varying light is linearly decreased with time.

3. The light supply method according to claim 2, wherein illuminance generated by the first fixed light is maintained between 9 lux and 11 lux.

4. The light supply method according to claim 2, wherein a color temperature of the first time-varying light, a color temperature of the second time-varying light, and a color temperature of the first fixed light are maintained between 1800 K and 2000 K.

5. The light supply method according to claim 2, further comprising:
    not providing a light in a fourth time interval between the third time interval and a first time interval of a next period by the light source module.

6. The light supply method according to claim 1, further comprising:
    reducing intensities of lights within a wavelength range shorter than 455 nanometers.

7. The light supply method according to claim 1, wherein a color temperature of the first time-varying light is linearly increased with time, and a color temperature of the second time-varying light is linearly decreased with time.

8. The light supply method according to claim 7, wherein a color temperature of the first fixed light is maintained between 3600 K and 5000 K.

9. The light supply method according to claim 7, further comprising: providing a fourth driving signal in a fourth time interval between the third time interval and a first time interval of a next period by the driver and providing a second fixed light by the light source module in response to the fourth driving signal, wherein the second time-varying light is gradually changed into the second fixed light upon the third time interval ending.

10. The light supply method according to claim 9, wherein a color temperature of the second fixed light is maintained between 1600 K and 2400 K.

11. The light supply method according to claim 9, wherein illuminance generated by the first time-varying light, illuminance generated by the second time-varying light, illuminance generated by the first fixed light, and illuminance generated by the second fixed light are maintained between 50 lux and 52 lux.

12. The light supply method according to claim 9, further comprising:
    reducing intensities of lights within a wavelength range shorter than 455 nanometers for the second fixed light.

13. The light supply method according to claim 1, wherein a time length of the second time interval is greater than or equal to a maintaining time of each step of the first time-varying light.

14. The light supply method according to claim 1, wherein a color temperature of the first fixed light is maintained between 3600 K and 5000 K.

15. The light supply method according to claim 1, further comprising: providing a fourth driving signal in a fourth time interval between the third time interval and a first time interval of a next period by the driver and providing a second fixed light by the light source module in response to the fourth driving signal, wherein the second time-varying light is gradually changed into the second fixed light upon the third time interval ending.

16. The light supply method according to claim 15, wherein a color temperature of the second fixed light is maintained between 1600 K and 2400 K.

17. The light supply method according to claim 15, wherein illuminance generated by the first time-varying light, illuminance generated by the second time-varying light, illuminance generated by the first fixed light, and illuminance generated by the second fixed light are maintained between 50 lux and 52 lux.

18. The light supply method according to claim 15, further comprising:
   reducing intensities of lights within a wavelength range shorter than 455 nanometers for the second fixed light.

* * * * *